(12) United States Patent
Verhoeven et al.

(10) Patent No.: US 9,566,387 B2
(45) Date of Patent: Feb. 14, 2017

(54) SYRINGE WITH ALTERNATIVELY SELECTABLE GRADUATIONS

(71) Applicant: VLOW Medical B.V., Eindhoven (NL)

(72) Inventors: Franciscus Maria Verhoeven, Eindhoven (NL); Andreas Adrianus Lambertus van den Houdt, Eindhoven (NL); Angelinus Quirinus Maria de Beer, Eindhoven (NL)

(73) Assignee: VLOW Medical B.V. (NL)

( * ) Notice: Subject to any disclaimer, the term of this patent is extended or adjusted under 35 U.S.C. 154(b) by 2 days.

(21) Appl. No.: 14/322,454

(22) Filed: Jul. 2, 2014

(65) Prior Publication Data
US 2015/0094667 A1 Apr. 2, 2015

(30) Foreign Application Priority Data

Jul. 4, 2013 (NL) .................................. 2011094

(51) Int. Cl.
*A61M 5/315* (2006.01)
*A61M 5/31* (2006.01)

(52) U.S. Cl.
CPC ....... *A61M 5/3135* (2013.01); *A61M 5/31505* (2013.01); *A61M 5/31526* (2013.01); *A61M 5/31536* (2013.01); *A61M 5/31568* (2013.01); *A61M 5/31573* (2013.01); *A61M 5/31581* (2013.01); *A61M 5/31595* (2013.01);
(Continued)

(58) Field of Classification Search
CPC .. A61M 5/31; A61M 5/3135; A61M 5/31511; A61M 5/31501; A61M 5/31505; A61M 5/31533; A61M 5/31526; A61M 5/31528; A61M 5/31525; A61M 5/31545; A61M 5/31548; A61M 5/3155; A61M 5/3156; A61M 5/31536; A61M 2005/3125; A61M 2005/3126
See application file for complete search history.

(56) References Cited

U.S. PATENT DOCUMENTS 2,432,605 A 12/1947 Barach
4,466,426 A * 8/1984 Blackman ........... A61M 5/3158
600/5

(Continued)

FOREIGN PATENT DOCUMENTS

EP 2201973 6/2010
GB 2495916 A * 5/2013 .............. A61M 5/31
(Continued)

*Primary Examiner* — Imani Hayman
*Assistant Examiner* — James D Ponton
(74) *Attorney, Agent, or Firm* — Patterson Intellectual Property Law PC

(57) ABSTRACT

The invention relates to a syringe having a longitudinal axis and comprising a barrel assembly including a barrel extending longitudinally between a proximal end and a distal end, and a collar provided at the proximal end of the barrel and defining a reading window. The syringe also comprises a plunger including a longitudinally extending graduation portion that is at least partially longitudinally slidably received in the barrel, and that provides for at least two mutually different visually readable graduations, wherein respective graduations extend along the longitudinal axis and are alternatively selectable by rotation of the graduation portion around the longitudinal axis, such that a selected graduation is visible through the reading window when the plunger is slid into and out of the barrel during use.

23 Claims, 4 Drawing Sheets

(52) U.S. Cl.
CPC ............... *A61M 2005/3126* (2013.01); *A61M 2005/31508* (2013.01)

(56) References Cited

U.S. PATENT DOCUMENTS

| | | | | |
|---|---|---|---|---|
| 5,376,081 A | * | 12/1994 | Sapienza | A61M 5/3129 604/186 |
| 2004/0024368 A1 | | 2/2004 | Broselow | |
| 2011/0015576 A1 | * | 1/2011 | Plumptre | A61M 5/31551 604/189 |
| 2011/0046559 A1 | | 2/2011 | Lum | |

FOREIGN PATENT DOCUMENTS

| | | |
|---|---|---|
| WO | 2010139644 | 12/2010 |
| WO | 2012050511 | 4/2012 |
| WO | 2013126173 | 8/2013 |

\* cited by examiner

SYRINGE WITH ALTERNATIVELY SELECTABLE GRADUATIONS

TECHNICAL FIELD

The present invention relates to a dosage device, and more in particular a syringe suitable for, inter alia, the injection of fluids in medical applications, and the dosing chemicals in non-medical applications.

BACKGROUND

Botulinum toxin type A, popularly known by one of its tradenames, Botox, is a protein and neurotoxin that is used in various cosmetic and medical procedures. In cosmetic applications, a botulinum toxin injection may be used to prevent the development of wrinkles by paralyzing facial muscles. In non-cosmetic applications, botulinum toxin may be used to treat conditions of excessive and inappropriate muscle contraction, spasticity (persistent states of muscle contraction), sphincter contraction, eye-movement disorders, tics and tremors.

Before the botulinum toxin can be administered to a patient by means of an injection, a clinician must reconstitute the botulinum toxin supplied by the manufacturer with a diluent, typically a saline solution. The botulinum toxin is normally supplied by the manufacturer in a vial containing a certain number of 'units', e.g. 50 units or 100 units, which vial comes with an instruction to dilute it with a certain volume of diluent, e.g. 1.25, 2.0, 2.5 or 5.0 ml. For instance, in case a 50-unit vial is to be diluted with 1.25 ml of saline solution, the resulting mixture comprises 4 units per 0.1 ml. When the same 50-unit vial is diluted with 2.0 ml or 2.5 ml of saline solution, the resulting mixture comprises 2.5 units per 0.1 ml and 2 units per 0.1 ml, respectively. The prescribed mixture ratio may vary with each manufacturer, and the treatment to be carried out with the final solution.

Importantly, a treatment with botulinum toxin may typically be defined in terms of a number of units, e.g. 1-5 units, to be injected across various sites of a body region to be treated. A chronic migraine treatment may, for example, prescribe that 5-unit injections are to be administered across seven different head/neck muscles.

BRIEF SUMMARY

Syringes used to administer botulinum toxin injections are normally provided with a barrel graduated in milliliters (ml). This means that clinicians must continuously make conversions between units and milliliters when they carry out a treatment. For instance, when a clinician has prepared a mixture with a mixture ratio of 4 units per 0.10 ml while the graduation on the barrel of the syringe indicates that it currently holds 3.2 ml of this mixture, and the treatment prescribes that a 5 unit injection must be given, then the clinician must calculate that the injection must be stopped when there is $(3.2-(5*(0.10/4))=3.075\approx)$ 3.1 ml of mixture left in the barrel. This practice of using a milliliter graduated barrel and making calculations during the treatment in not only inconvenient, it also increases the risk of reading and computational errors. In addition, it requires the clinician to closely monitor the graduation on the barrel instead of the patient as he administers the toxin, which is undesirable.

It is therefore an object of the invention to provide for a syringe that facilitates the administration of unit injections, and in particular for units of different sizes. It is a further object of the invention to provide for a syringe that allows a clinician to focus his attention on the patient instead of the syringe during such administration.

To this end, a first aspect of the present invention is directed to a syringe having a longitudinal axis. The syringe may comprise a barrel assembly, which may include a barrel that extends longitudinally between a proximal end and a distal end, and a collar that is provided at the proximal end of the barrel and defines a reading window. The syringe may also comprise a plunger, which may include a longitudinally extending graduation portion that is at least partially longitudinally slidably received in the barrel, and that provides for at least two mutually different visually readable graduations, which respective graduations extend along the longitudinal axis and are alternatively selectable by rotation of the graduation portion around the longitudinal axis, such that a selected graduation is visible through the reading window when the plunger is slid into and out of the barrel during use.

The presently disclosed syringe does not offer a single milliliter graduation to assess the current mixture content of the barrel, but instead a plurality of alternatively selectable graduations. These graduations may preferably have units or graduation or graduation increments that correspond to different commonly used mixture ratio's or volume units. For instance, a mixture ratio of 4 units per 0.1 ml amounts to a volume unit of 0.025 ml, whereas the ratio of 2.5 units per 0.1 ml corresponds to a volume unit of 0.04 ml, and a ratio of 2 units per 0.1 ml corresponds to a volume unit of 0.05 ml. These volume units (0.025 ml, 0.04 ml and 0.05 ml) are currently compatible with most botulinum toxin brands that are approved for sale in the US and the EU. Accordingly, a plunger having a graduation portion that provides for three graduations having a unit of graduation or graduation increment of respectively 0.025 ml, 0.04 ml and 0.05 ml conveniently allows a single syringe to be used in practically all accepted botulinum toxin treatments.

In preparation of a treatment, a clinician may first prepare the diluted botulinum toxin mixture with a certain mixture ratio (e.g. 4 units per 0.1 ml), and then fill the barrel of the syringe—with a corresponding graduation selected (e.g. a graduation having a unit of graduation or graduation increment of 0.025 ml)—with this mixture. In the reading window of the collar, he may observe the number of units that are contained in the barrel at any moment, both during the filling of the barrel and during the subsequent treatment. As the number of units left in the barrel is immediately visible in the reading window, the need to perform any elaborate calculations/conversions during the treatment is overcome. All that is required now is that the clinician determines the final content of the barrel in units before he administers an injection. For instance, if the initial content of the barrel is 10 units, and the treatment prescribes that a 4 unit injection must be given, then the clinician need merely compute that the injection must be stopped when there are (10−4=) 6 units left in the barrel. The adaptability of the graduation to the mixture ratio that is being used, and the resulting simplification of the computation required from the clinician during treatment facilitate the accurate administration of unit injections, and reduce the risk of reading and computational errors.

To further allow a clinician to focus on the patient instead of the syringe, the latter may be provided with means for auditive and/or tactile feedback that inform the clinician—during the administration of an injection—of unit-wise progress. That is, the means for auditive and/or tactile feedback may be configured to produce an audible sound, e.g. a click, and/or an increase in sliding resistance each time during the injection when another unit volume has been discharged from the syringe.

These and other features and advantages of the invention will be more fully understood from the following detailed description of certain embodiments of the invention, taken together with the accompanying drawings, which are meant to illustrate and not to limit the invention.

DETAILED DESCRIPTION

Figure 1A:
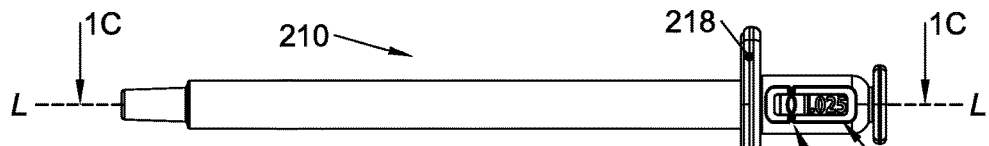
FIG. 1A is a schematic front view of an exemplary embodiment of a syringe according to the present invention.
Figure 1B:
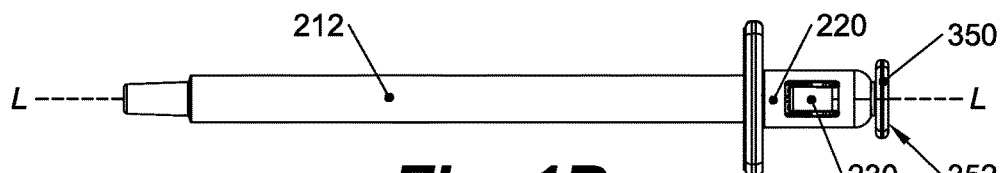
FIG. 1B is a schematic back view of the syringe shown in FIG. 1A.
Figure 1C:
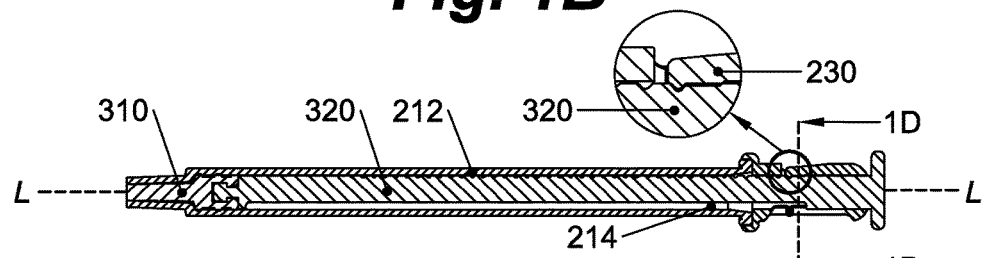
FIG. 1C is a schematic longitudinal cross-sectional side view of the syringe shown in FIGS. 1A-1B, taken along line 1C-1C in FIG. 1A.
Figure 1D:
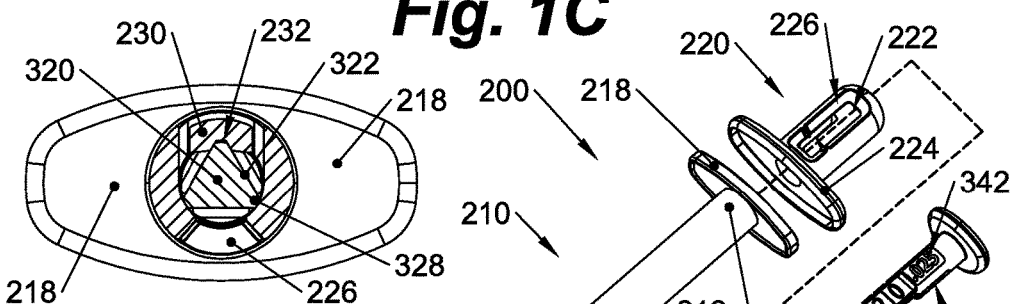
FIG. 1D is a schematic transverse cross-sectional side view of the syringe shown in FIGS. 1A-1C, taken along line 1D-1D in FIG. 1C.
Figure 2:
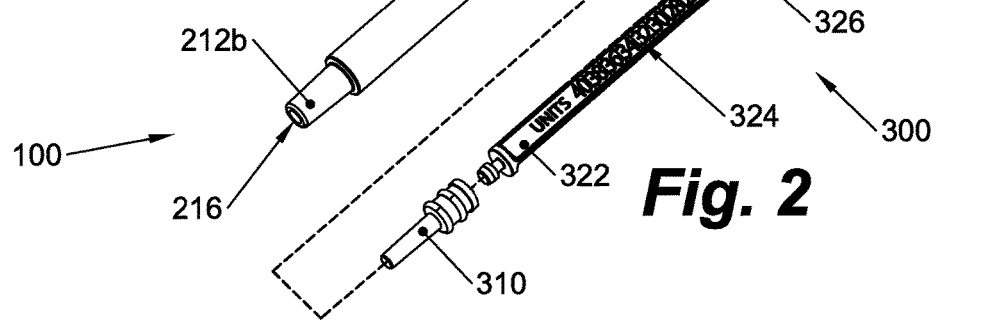
FIG. 2 is a schematic exploded view the syringe shown in FIGS. 1A-1D.
Figure 3:
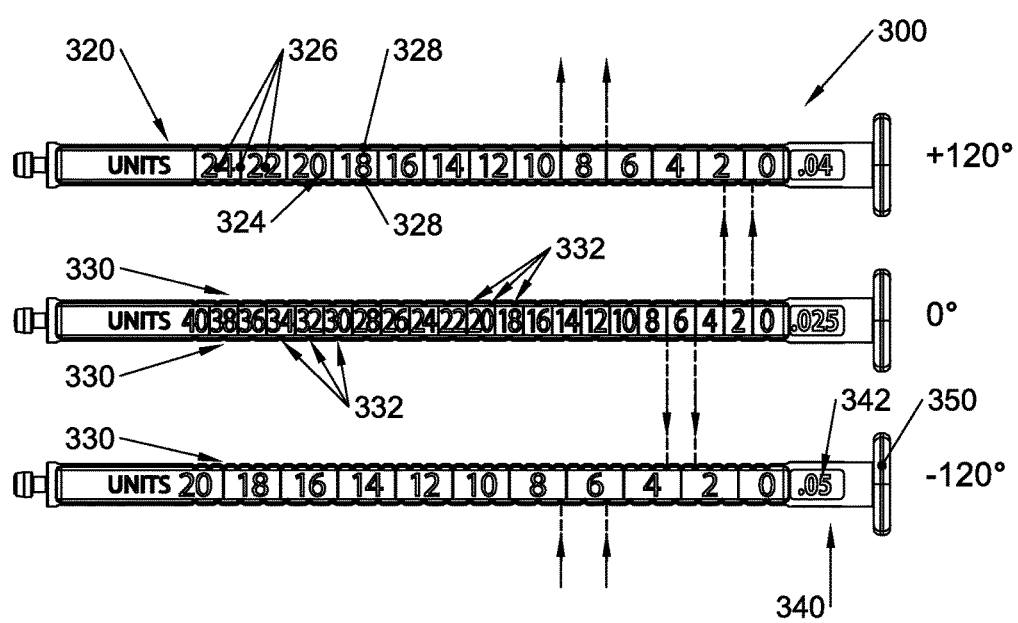
FIG. 3 illustrates three schematic front views of the plunger of the syringe shown in FIGS. 1A-1D and FIG. 2.

FIGS. 1-3 schematically illustrate an exemplary embodiment of a syringe 100 according to the present invention. Below, the presently disclosed syringe will be described in general terms, where appropriate with reference to FIGS. 1-3.

The syringe 100 according to the presently disclosed invention may include a barrel assembly 200 and a plunger 300.

The barrel assembly 200 may include a barrel 210 and a collar 220. The barrel 210 and the collar 220 may be manufactured separately and optionally releasably connected first during assembly, or be integrally formed. Both the barrel 210 and the collar 220 may be made from plastic, for instance through injection molding.

The barrel 210 may include an elongate tubular, e.g. cylinder jacket-shaped, body 212 that extends along a longitudinal axis L of the syringe 100, between a proximal end 212a and a distal end 212b, and that defines a central bore 214 in which the plunger 300 is at least partially slidably and rotatably receivable. At its proximal end 212a, the barrel body 212 may be provided with two finger wings 218 to allow a clinician to press an extended plunger into the bore 214 of the barrel 210 with a thumb, while supporting two fingers distally against the finger wings 218 in a conventional manner of syringe operation. The finger wings 218 may also serve to facilitate attachment of the collar 220 to the barrel body 212. At the distal end 212b of the barrel body 212, the central bore 214 may end in a fluid port 218 through which fluid may be drawn into and/or ejected from the bore 214. The distal end 212b of the barrel body 212 itself may taper into a hollow tip, which may provide a point of attachment for a needle (not shown). The tip may be of any suitable type, and for instance be a Luer-Slip tip—as shown in the Figures —, a Luer-Lock tip or an eccentric tip.

The barrel body 212 of the exemplary embodiment shown in the Figures is opaque. In different embodiments, however, the barrel body 212 may be transparent to enable a clinician to visually assess the contents of the barrel bore 214, for instance to confirm a state/condition or identity of a fluid contained therein. In embodiments featuring a transparent barrel body 212, the barrel body 212 may be provided with a volume graduation, for instance in milliliters.

The collar 220 may be connected to the proximal end 212a of the barrel body 212, such that a plunger passage 222 defined by the collar 220 is in alignment with the central bore 214 of the barrel 210. At its distal end the collar 220 may define a base 224, which may be shaped complementarily to the finger wings 218 at the proximal end 212a of the barrel body 212, and which may serve to facilitate attachment of the collar 220 thereto.

At its front side the collar 220 may further define a reading window 226 through which a clinician can see the plunger 300, and more in particular a selected graduation 324 provided on the graduation portion 320 of the plunger 300, and, optionally, a volume unit indication 342 provided by a volume unit indication portion 340 of the plunger 300, as will be described infra. Structurally, the reading window 226 may be a suitably dimensioned aperture in a wall of the collar 220 that enables a view into the plunger passage 222. Here, 'suitably dimensioned' means that the dimensions of the aperture may be tailored to the configuration of in particular the graduation portion 320 of the plunger 300, so that, when a certain graduation 324 is selected by rotation of the plunger 300 relative to the barrel 210, only that selected graduation 324 is visible through the reading window 226. In one embodiment, the reading window 226 may be provided with a window pane, in particular in the form of a magnifying lens to facilitate reading of a selected graduation 324 and/or a corresponding volume unit indication 342 on the plunger 300. In another embodiment, the edge or margin of the reading window may be provided with an index 228, e.g. a notch, that may align with successive graduation marks 326 of a selected graduation 324 when the plunger 300 is slid into and out of the barrel 210 during use.

The collar 220 may preferably be opaque in order to enhance the (visual) selection function of the reading window 226.

The plunger 300 may include a sealing element 310, a graduation portion 320, a volume unit indication portion 340, and a handle 350.

The sealing element 310, which may be made of a suitably flexible and fluid impermeable material, may be attached to a distal end of the graduation portion 320 of the plunger 300, and be dimensioned to enable slidable, sealing contact with an inner wall of the central bore 214 of the barrel 210. The fluid port 216, an inner wall of the central bore 214 and the sealing element 310 may thus delimit a portion of the central bore 214 that serves as a fluid chamber configured to contain a fluid to be delivered by the syringe 100. The size of the fluid chamber may be varied by slidably displacing the plunger 300 relative to the barrel 210. This way, the fluid chamber can be varied in size from virtually zero to nearly the entire volume of the central bore 214.

The graduation portion 320 of the plunger 300 may preferably comprise a longitudinally extending, generally prismatic body. Here 'generally prismatic' may be construed to refer to both truly prismatic bodies having planar faces/sides, and bodies that are only approximately prismatic, for instance because their faces are slightly convexly or concavely curved and/or because their longitudinal edges/corners are rounded off. It is noted that the generally prismatic body of the graduation portion 320 may be connected to/integrated with other plunger parts 310, 340 at its ends, such that its bases (i.e. its distal and proximal on end faces) may lie within the plunger 300, and may not be free; these on end faces may therefore be disregarded in the determination of whether the graduation portion 320 includes a generally prismatic body. The prism reflected by the generally prismatic body may typically be a regular right prism. As is best seen in the transverse cross-section of FIG. 1D, the graduation portion 320 of the plunger 300 of the depicted syringe 100 of FIGS. 1A-3 comprises a generally triangular prismatic body (having a generally triangular cross-section). In other embodiments, however, the graduation portion 320 may comprise a generally prismatic body of a different type, e.g. a tetragonal or pentagonal prismatic body (having a generally tetragonal or pentagonal cross-section, respectively), or even a non-prismatic body, e.g. a cylindrical body or a body with an elliptical cross-section.

The graduation portion 320 may provide for at least two mutually different, visually readable graduations 324, which graduations 324 may extend in parallel along the longitudinal axis L of the syringe 100. In case the graduation portion 320 has a generally prismatic shape, each of the graduations 324 may be exclusively associated with one of its longitudinally extending faces 322. Each graduation 324 may, for instance, be printed on one of these faces 322, as in the depicted embodiment (see FIGS. 2-3). Furthermore, these graduations 324 may have mutually different graduation increments to form mutually different graduated measuring scales.

Each graduation 324 may include a plurality of longitudinally spaced apart graduation marks 326, for instance in the form of transversely or tangentially extending graduation lines and/or numerical marks. Seen along the longitudinal axis, from its proximal end to its distal end, any numerical marks on the graduation may be arranged in ascending order. In the depicted embodiment of FIGS. 1A-3, each graduation 324 includes a plurality of longitudinally spaced apart transverse graduation lines, which are separated from one another by numerical marks (see FIGS. 2 and 3).

The graduation increment of a respective graduation 324, i.e. the volume that corresponds to the distance between any two adjacent graduation marks 326, may preferably be a volume unit (for instance of 0.01, 0.02, 0.025, 0.04 or 0.05 ml) in integer multiples of which a treatment that is intended to be carried out with the syringe 100 is conventionally described. Accordingly, the graduations 324 do preferably not contain a combination of major and minor graduation marks, wherein the minor graduation marks subdivide a unit of graduation or volume unit, defined by adjacent major graduation marks, into smaller sub-volume units. The graduation increments of the alternatively selectable graduations 324 may differ, so as to allow the syringe 100 to be conveniently used in various treatments described in terms of different volume units.

In an advantageous embodiment of the syringe 100, the graduations 324 may be adapted to facilitate botulinum toxin injections, such that the respective graduation increments reflect common volume units used in administering such injections. As described above, the volume units 0.025 ml, 0.04 ml and 0.05 ml—which correspond to botulinum toxin/saline-mixture ratio's of, respectively, 4 units per 0.1 ml, 2.5 units per 0.1 ml, and 2 units per 0.1 ml—are currently compatible with most botulinum toxin brands that are approved for sale in the US and the EU. Accordingly, a plunger 300 having a graduation portion 320 that provides for three graduations 324 having graduation increments of respectively 0.025 ml, 0.04 ml and 0.05 ml conveniently allows a single syringe 100 to be used in practically all accepted botulinum toxin treatments.

The syringe 100 in the depicted embodiments is configured to facilitate treatments involving botulinum toxin injections. To this end, the graduation portion 320 of the plunger 300 provides for three alternatively selectable graduations 324, having graduation increments of, respectively, 0.025 ml, 0.04 ml, and 0.05 ml. For each graduation 324, the distance between any two adjacent graduation lines corresponds to two volume units, while the numerical value centered in between each two adjacent graduation lines corresponds to the number of volume units present/left in the fluid chamber when the index 228 of the reading window 226 is halfway the two graduation lines. Accordingly, the distance between two adjacent graduation marks 326, i.e. the distance between a graduation line and a center of a numerical unit mark, corresponds to one volume unit.

The volume unit indication portion 340 of the plunger, which may be arranged at the proximal end of the graduation portion 320, may provide, for each graduation 324, a visually readable volume unit indication 342. Each volume unit indication 342 may include a numerical value that represents the magnitude of the volume unit in milliliters (or another suitable unit), be arranged in longitudinal alignment with the respective graduation 324, and preferably be visible through the reading window 226 when the plunger 300 is maximally pushed into the barrel (see FIG. 1A), all such that the clinician using the syringe 100 can quickly determine which graduation is selected.

In one embodiment, the graduations 324 and/or their associated volume unit indications 342 may be provided in different colors, e.g. red, green and blue, to facilitate their quick recognition.

Figure 6:
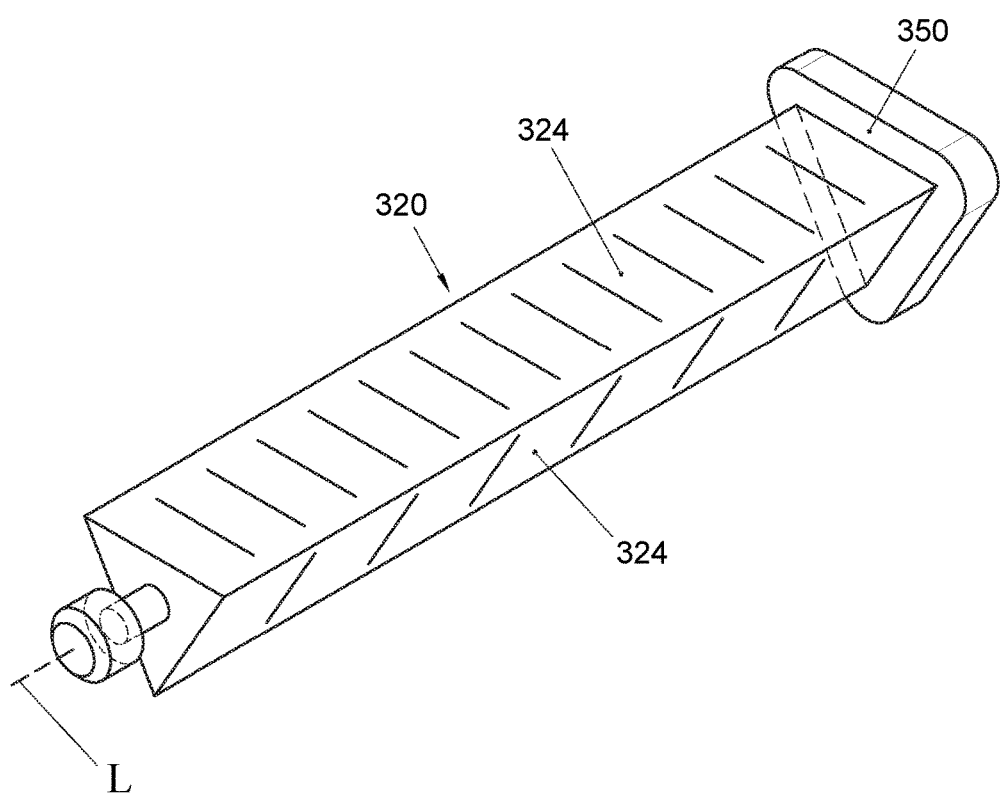
FIG. 6 shows a schematic view of an embodiment of a plunger.

The handle 350 of the plunger 300 may be provided at the proximal end of the plunger, and, at its proximal end, provide a support surface 352 for a finger or thumb. In particular when the graduation portion 320 of the plunger 300 includes a generally prismatic body, the handle 350 may be similar in shape, i.e. be similarly prismatic, or at least have a similar transverse cross-section as the graduation portion 320, so as to define a number of faces or sides that corresponds to the number of faces 322 and graduations 324 on the graduation portion 320 (see for instance FIG. 6). The faces 322 of the graduation portion 320 may then be longitudinally aligned with the faces of the handle 350, so that holding the handle 350 while selecting a graduation 324 on the graduation portion 320 provides tactile confirmation as to the rotational orientation of the plunger 300 and the graduations 324 thereon.

At least part of the plunger 300 may be both longitudinally slidably and rotatably received in the central bore 214 and the plunger passage 222 of the barrel assembly 200. A longitudinal sliding motion of the plunger 300 in and relative to the barrel assembly 200 may increase or decrease the volume of the fluid chamber, and thus enable aspiration or ejection of fluid into or from the barrel bore 214. A (tangential) rotation of the plunger 300 around the longitudinal axis L of the syringe 100, and relative to the barrel assembly 100, may serve to select one of the graduations 324 provided on the graduation portion 320 of the plunger 300 for use. The selected graduation 324 is the one graduation that is visible through the reading window 226 in the collar 220, in particular when the plunger 300 is longitudinally slid into and out of the barrel assembly 200 during use.

To ensure that a selected graduation 324 cannot not be accidentally changed during use, a rotational locking mechanism may be provided. The mechanism may be configured to lock the plunger 300 in its rotational (but not its longitudinal) position relative to the barrel assembly 200 when one of the graduations 324 is selected. The rotational locking mechanism may include formations or structures that are provided by the plunger 300 and the barrel assembly 200, respectively, and that are configured to engage each other, for instance in a resilient snap type action, when the plunger 300 is rotated around the longitudinal axis L relative to the barrel assembly 200, into a rotational position in which a graduation 324 is selected, so as to releasably rotationally lock the plunger 300 in the respective rotational position. Typically, the formations of at least one of the plunger 300 and the barrel assembly 200 may be flexible and resilient in nature.

As in the depicted embodiment of FIGS. 1A-3, first formations may be provided by the plunger 300 in the form of the longitudinally extending, possibly rounded edges 328 of the generally prismatic graduation portion 320 of the plunger 300. A second formation may be provided by the collar 220 in the form of a resilient finger 230, for instance disposed at the back of the collar 220 (see FIG. 1B). At an inward facing surface 231, the resilient finger 230 may be provided with a longitudinally extending recess 232 (see FIG. 1D) in which the longitudinal first formations/edges 328 are alternatively receivable. The configuration may be such that, when, in use, the plunger 300 is rotated relative to the barrel assembly 200 to select one of the graduations 324, the longitudinal edge 328 of the graduation portion 320 opposite to/behind the face 322 providing the respective graduation 324 is rotated into contact with the resilient finger 230. Just before the respective graduation 324 is properly selected and the associated longitudinal edge 328 is fittingly received in the longitudinal recess 232 in the resilient finger 230, the clinician performing the selection must exert some rotational force to have the longitudinal edge 328 push the resilient finger 230 radially outward, so as to enable the edge 328 to rotate into rotational alignment with the recess 232. Once the edge 328 is in alignment with the recess 232, the resilient finger 230 may snap back into place, releasably locking the rotational position of the plunger 300 relative to the barrel assembly 200. It will be clear that the plunger 300 may be unlocked by forcefully further rotating it relative to the barrel assembly 200 in a similar manner.

It is appreciated that, although FIGS. 1A-3 show an embodiment of a syringe 100 in which a longitudinal extending first formation 328 is defined by the plunger 300 and a second formations 230, 232 is defined by the barrel assembly 200 (see especially FIG. 1D), the barrel assembly 200 may define at least one longitudinal extending first formation 213, while the plunger 300 may define one or more second formations 329 for engaging said first formation 213 defined by the barrel assembly 200 when the plunger 300 is rotated around the longitudinal axis L, into a rotational position in which a graduation 324 is selected, so as to releasably lock the plunger 300 in the respective rotational position.

To further allow a clinician to focus on the patient instead of the syringe 100, the latter may be provided with means for auditive and/or tactile feedback that inform the clinician—during the administration of an injection—of unit-wise progress. That is, the means for auditive and/or tactile feedback may be configured to produce an audible sound, e.g. a click, and/or an increase in sliding resistance each time during the injection when another unit volume has been discharged from the syringe 100.

To this end, each of the graduations 324 may be exclusively associated with a plurality of longitudinally spaced apart increment formations 330, 215. The pluralities of increment formations 330 may be provided by the graduation portion 320 of the plunger 300 (as in the depicted embodiment of FIGS. 1A-3), or the pluralities of increment formations 215 may be provided by the barrel assembly 200, e.g. at inner wall surfaces 214b of the central bore 214 and the plunger passage 222. The increment formations 332 of each plurality of increment formations 330, which may typically take the form of indentations or protrusions, may be equidistantly spaced apart, such that a longitudinal distance between two longitudinally adjacent increment formations 332 of a respective plurality of increment formations 330 corresponds to the graduation increment of the associated graduation 324, or at least to an integer multiple or integer fraction thereof.

FIG. 3 schematically illustrates the plunger 300, and more specifically the triangularly prismatic graduation portion 320 of the plunger 300, of the exemplary embodiment in three rotational positions. The rotational position of the plunger 300 in the middle is labeled 0°, while the rotational positions shown above and below it are obtained through a rotation of the plunger 300 from this middle position through an angle of, respectively, +120° and −120° around the longitudinal axis L. The respective graduation 324 that is visible in each of the rotational positions of the plunger 300 is associated with a respective plurality of longitudinally spaced apart increment formations 322 in the form of indentations 332, which indentations are provided in the longitudinal edge 328 of the triangular prismatic graduation portion 320 that is opposite to/lies behind the face 322 on which the respective graduation 324 is provided. —Indeed, this relation between a respective graduation 324, the face 322 of the prismatic graduation portion 320 on which it is provided, and a respective edge 328 of the prismatic graduation portion 320 is advantageously the same as that employed for the rotational locking mechanism described above. —Accordingly, the plurality of longitudinally spaced apart increment formations 330 and the graduation 324 that is associated therewith are each time visible in two respective front views/rotational positions of the plunger 300 in FIG. 3. For clarity, two transversely extending graduation lines on each graduation 324 (which graduation lines are spaced two volume units apart!) are schematically connected to two indentations 332 on the associated longitudinal edge 328 by means of dashed and arrowed lines, extending from the respective graduation 324 to the respective indentations 332.

Figure 4:
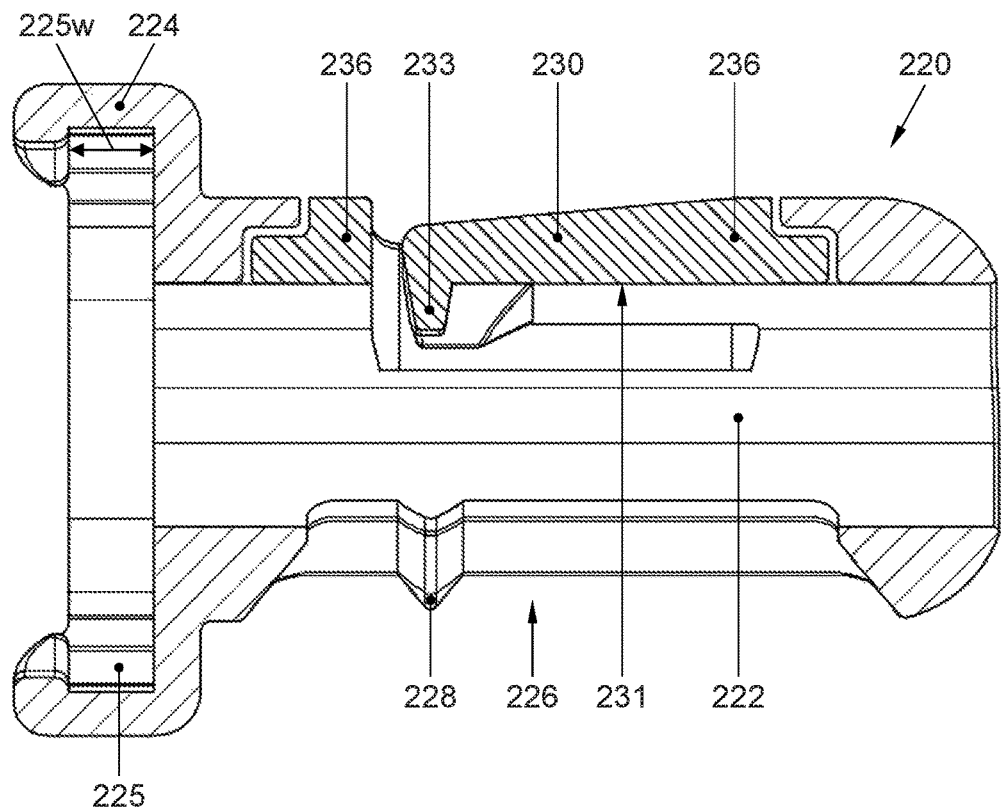
FIG. 4 is a schematic longitudinal cross-sectional side view of an alternative embodiment of a collar of an alternative embodiment of a syringe according to the present invention.
Figure 5:
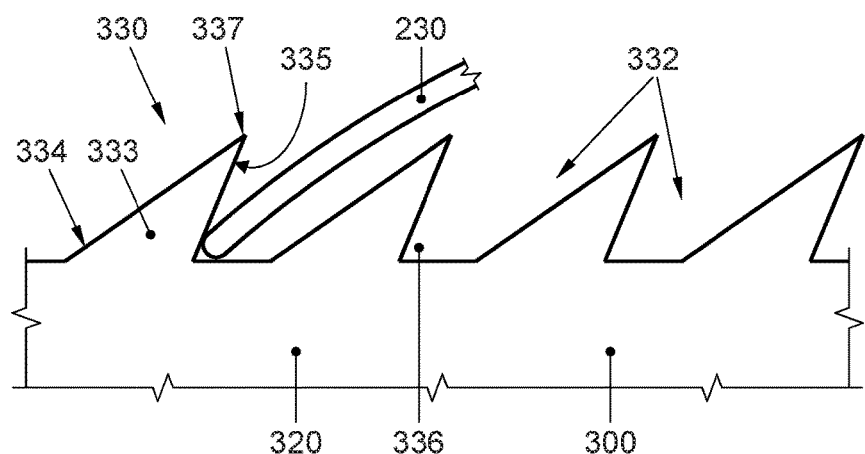
FIG. 5 shows a schematic detail of a schematic longitudinal cross sectional side view of an embodiment of a plurality of longitudinal spaced apart increment formations and an embodiment of an index formation according to the present invention.

The pluralities of longitudinally spaced apart increment formations 330 may be configured for cooperation with an index or counter formation provided by the barrel assembly 200, in case the pluralities of increment formations are provided by the plunger 300 (as in the depicted embodiment of FIGS. 1A-3), or the index or counter formation 327 may be provided by the plunger 300, in case the pluralities of increment formations 215 are provided by the barrel assembly 200. As in the depicted embodiment of FIGS. 1A-3, for instance, the collar 220 of the barrel assembly 200 may include a resilient index formation, e.g. in the form of a resilient finger 230 (that also serves as part of the rotational locking mechanism described above), that is configured to periodically engage the increment formations 332 of the plurality increment formations 330 associated with a respective selected graduation 324 when the plunger 300 is slid into and out of the barrel 210 during use, so as to periodically increase resistance to the longitudinally sliding motion and/or to periodically produce an audible sound. To enable proper engagement with the indentations 332 on the plunger 300, an inner surface 231 of the resilient finger 232 may, for example, define a protrusion 233 such as a transversely extending ridge (as is for example depicted in FIG. 4) that is configured to periodically snap into the indentations 332 during sliding motion of the plunger 300 relative to the barrel 210.

In the depicted embodiment of FIGS. 1A-3, the plunger 300 provides for the pluralities of longitudinally spaced apart increment formations 330, while the barrel assembly 200 provides for a single index formation 230 that is configured for alternative engagement with any of them. It is understood that the configuration may be the other way around in an alternative embodiment. In such an embodiment, the barrel assembly 200, in particular inner surfaces of the central bore 214 and/or the plunger passage 222, may be provided with pluralities of longitudinally spaced apart increment formations, one for each graduation 324 on the plunger 300, and tangentially spaced apart by for instance (360/n)°, with n the number of graduations 324. The plunger 300 may then be provided with a complementary formation, in particular near its distal end, that is arranged such that it is in rotational registry with a certain plurality of increment formations on the barrel assembly 200 when the graduation 324 associated with said plurality 330 is selected.

In embodiments, the syringe 100 can be arranged to move the plunger 300 backwardly to at least some extent after a user, who has pushed the plunger 300 forwardly until the index formation 230 engaged a subsequent increment formation 332 during use of the syringe 100, releases the plunger 300. It is noted that the backward direction can extend from the distal end 212b towards the proximal end 212a and along the longitudinal axis L. For example, the length along which the plunger 300 can be moved backwardly may be smaller than 25%, preferably smaller than 15%, more preferably smaller than 10%, such as for instance at most 5%, of the length between two adjacent increment formations 332 seen in the axial direction of the syringe 100. Advantageously, said length between said two adjacent increment formations 332 may for instance be the length between two adjacent increment formations 332 of the respective plurality 330 of increment formations 332 being engaged by the index formation 230.

An advantageous effect of arranging the syringe 100 such that it can move the plunger 300, which is released by the user, backwardly to some extent, e.g. at least partly under action of a liquid, for instance a botulinum toxin, provided in the barrel 210, which liquid may have become pressurized to some extent when the user administered the yet last unit, may be that the plunger 300 can be pushed backwardly thereby increasing the space in the barrel 210 which accommodates the liquid. Hence, the liquid can depressurize to some extend and/or it can be counteracted that a drip exits the fluid port 216 and/or a needle (not shown) attached to the barrel 210 after the yet last unit have been administered. Advantageously, the syringe 100 may thus be arranged to provide for a kind of "suck back" action during use in order counteract that a drop may unintentionally follow the administered unit.

Alternatively or additionally, an effect of arranging the syringe 100 such that it can move the plunger 300 released by the user backwardly to some extent can be that the syringe can provide a relatively good auditive and/or tactile feedback to the user.

Another advantageous effect may be that only a relatively small force may be needed in order towards move the plunger 300 to the next increment formation 332, e.g. towards the next "click". Additionally or alternatively, an effect can be that said arrangement of the syringe 100 can counteract that the plunger 300 will be unintentionally pushed beyond the intended engaging increment formation 332 towards the following increment formation 332, e.g. thereby counteracting that two units are administered when administering of only one unit is intended.

In preferred embodiments, the index formation 230 may be movable with respect to the barrel body 212 in at least a direction parallel to the longitudinal axis L. It is noted that the length along which the index formation 230 may be movable can preferably be smaller than 25%, more preferably smaller than 15%, yet more preferably smaller than 10%, such as for instance at most 5%, of the length between two adjacent increment formations 332 seen in the axial direction of the syringe 100. For example, said length between two adjacent increment formations 332 can be the length between two adjacent increment formations 332 of that one of the pluralities 330 of longitudinally spaced apart increment formations in which the increment formations 332 are mutually spaced apart the least far, such as for instance the plurality 330 of longitudinally spaced apart increment formations corresponding to the smallest graduation increment.

For example, the index formation 230 can be movable with respect to the barrel body 212 at least partly due to that the index formation 230 is formed as a part of an index formation holding portion 236 which is movably held in the collar 220. Thereto, the index formation holding portion 236 and/or the collar 220 may be substantially shaped such as in the exemplary embodiment of FIG. 4, which shows a schematic longitudinal cross-sectional side view of an embodiment of a collar 220 of an embodiment of a syringe 100.

Alternatively or additionally, the index formation 230 can be movable with respect to the barrel body 212 at least partly due to that the index formation 230 is provided at the collar 220 and said collar 220 is axially movably connected to the barrel body 212. For example, the attachment of the collar 220 to the barrel body 212 may thereto be provided with some backlash or so-called clearance. For instance, seen in the longitudinal direction L, a width 225*w* of an interior space 225 in the base 224 may be wider than a width of a finger wing 218 held in said interior space 225 during use.

As can be seen in FIG. 5, which shows an exemplary embodiment of a plurality 330 of longitudinal spaced apart increment formations 332 and an exemplary embodiment of an index formation 230, the increment formations 332 may in embodiments be formed by indentations and/or protrusions. For example, the index formation 230 may form a serrated or toothed pattern.

It is noted that a front side of a protrusion 333, may comprise a backwardly sloping front surface 334, which may facilitate that the plunger 300 can be pushed forward by a user relatively easily. Additionally or alternatively, a rear side of a protrusion 333, may comprise a backwardly sloping rear surface 335. Said backwardly sloping rear surface 335 may provide for some space 336 to allow the plunger 300 to move backwardly to some extend after a user who has pushed the plunger 300 forwardly until the index formation 230 moves over a top portion 337 of the protrusion 333 of the increment formation 332 during use of the syringe 100. However, said backwardly sloping rear surface 335 may further counteract that the plunger 300 can unintentionally be moved backwardly too far.

Furthermore, it is noted that the increment formations 332, the graduation portion 320, or the plunger 300 can be made partly or substantially completely of a wear-resistant, hard or stiff material, such as metal or a metal alloy or a relatively wear-resistant, hard or stiff plastic material. Additionally, or alternatively, the protrusion 233 of the index formation 230, the index formation 230, or the movable index formation holding portion 236 can be made partly or substantially completely of a wear-resistant, hard or stiff material, such as metal or a metal alloy or a relatively wear-resistant, hard or stiff plastic material. By making said respective part or parts of the syringe 100 of said wear-resistant, hard or stiff material, the respective engaging parts of the index formation 230 and increment formations 332 can be relatively small and/or can be positioned relatively accurate, especially in comparison to one made of a relatively wear-prone, cheap and/or weak plastic material. Alternatively or additionally, by making the respective part or parts of a relatively wear-resistant, hard or stiff material, especially a metal or metal alloy, a relatively good auditive and/or tactile feedback can be provided.

Besides, the syringe 100 may be arranged such as to be brought into a mode in which the plunger 300 can be moved axially without the index formation 230 engaging the increment formations 332. Hence, the plunger 300 may be retracted and/or extended relatively easily, e.g. in order to suck up fluid, such as for instance botulinum toxin, in order to load the syringe 100.

For example, the plunger 300 can be rotated around the longitudinal axis L, into a rotational position in which the index formation 230 and/or its protrusion 233 are/is no longer directed into and/or towards a respective longitudinal edge 328 provided with the respective increment formations 332, but are/is directed substantially towards a respective longitudinally extending face 322. For example in case the graduation portion 320 has a generally triangular cross-section, the plunger 300 can be rotated over about 60° in order to be brought into a so-called running-free mode.

Alternatively or additionally, the syringe 100 can be of such design that the protrusion 233 of the index formation 230, the index formation 230, or the movable index formation holding portion 236 can temporarily be moved axially away from the plunger passage 222. The index formation 230, or the movable index formation holding portion 236 can thereto for instance be provided with a lever, for example such that when a user pushes at one side of the lever, another side of the lever, which can be provided with the increment formation engaging protrusion 233 of the index formation 230, moves away from the plunger passage 222 and/or the respective longitudinal edge 328 provided with the respective increment formations 332. Additionally or alternatively, the protrusion 233 of the index formation 230, the index formation 230, or the movable index formation holding portion 236 can be adjustable, e.g. in order to adjust a biasing force with which the protrusion 233 of the index formation 230, and/or the index formation 230 can be biased into the plunger passage 222, and/or towards the respective longitudinal edge 328 provided with the respective increment formations 332. Hence, for example the auditive and/or tactile feedback can be adjustable, and/or the sliding resistance can be adjustable, e.g. in order to increase and/or decrease it.

Although illustrative embodiments of the present invention have been described above, in part with reference to the accompanying drawings, it is to be understood that the invention is not limited to these embodiments. Variations to the disclosed embodiments can be understood and effected by those skilled in the art in practicing the claimed invention, from a study of the drawings, the disclosure, and the appended claims. Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, it is noted that particular features, structures, or characteristics of one or more embodiments may be combined in any suitable manner to form new, not explicitly described embodiments.

LIST OF ELEMENTS

100 syringe
200 barrel assembly
210 barrel
212 barrel body
212a,b proximal end (a) and distal end (b) of barrel body
214 central bore
216 fluid port
218 finger wings
220 collar
222 plunger passage
224 base
225 interior space in base
225w width of interior space
226 reading window
228 index
230 resilient finger/(index) formation
231 inner surface
232 longitudinal recess
233 protrusion
236 index formation holding portion
300 plunger
310 sealing element
320 graduation portion
322 face/side
324 visually readable graduation
326 graduation mark
328 longitudinal edge
330 plurality of longitudinally spaced apart increment formations
332 increment formation
333 protrusion
334 backwardly sloping front surface
335 backwardly sloping rear surface
336 space
337 top portion of protrusion
340 volume unit indication portion
342 visually readable volume unit indication
350 handle
352 finger/thumb support surface
L longitudinal axis

We claim:

1. A syringe having a longitudinal axis, comprising:
a barrel assembly including:
a barrel extending longitudinally between a proximal end and a distal end,
a collar provided at the proximal end of the barrel and defining a reading window;
a plunger including:
a longitudinally extending graduation portion that is at least partially longitudinally slidably received in the barrel, and that provides for at least two mutually different visually readable graduations, wherein respective graduations extend along the longitudinal axis and have mutually different graduation increments to form mutually different graduated measuring scales, and wherein the respective graduations are alternatively selectable by rotation of the graduation portion around the longitudinal axis, such that a selected graduation is visible through the reading window when the plunger is slid into and out of the barrel during use.

2. The syringe according to claim 1, wherein the graduation portion comprises a generally prismatic body with a plurality of faces, and wherein each of the graduations is exclusively associated with one of these faces.

3. The syringe according to claim 2, wherein the faces of the generally prismatic body of the graduation portion are connected at longitudinal edges, and
wherein each longitudinal edge of the generally prismatic body of the graduation portion defines a longitudinally extending first formation.

4. The syringe according to claim 1, wherein the plunger further includes a handle that is provided at a proximal end of the plunger, said handle being wider than a central bore in which the plunger is at least partially slidable, and said handle having a generally polygonal transverse cross-section defining a number of sides that corresponds to the number of graduations on the graduation portion.

5. The syringe according to claim 1, further comprising
at least one longitudinally extending first formation defined by one of the barrel assembly and the plunger; and
at least one second formation defined by the other of the barrel assembly and the plunger,
wherein said first and second formations are configured to engage one another when the plunger is rotated around the longitudinal axis, into a rotational position in which a graduation is selected, so as to releasably lock the plunger in the respective rotational position.

6. The syringe according to claim 5, wherein the at least one longitudinally extending first formation is at least partially defined by the graduation portion of the plunger.

7. The syringe according to claim 5, wherein the graduation portion comprises a generally prismatic body with a plurality of faces, and wherein each of the graduations is exclusively associated with one of these faces, wherein the faces of the generally prismatic body of the graduation portion are connected at longitudinal edges, and further wherein the collar defines said at least one second formation in the form of a resilient finger, an inner surface of which defines a longitudinal recess for reception of at least one of the longitudinal edges of the generally prismatic body of the graduation portion of the plunger.

8. The syringe according to claim 7,
wherein the resilient finger defined by the collar is configured to periodically engage the at least one longitudinally extending first formation when the plunger is rotated around the longitudinal axis into and out of a rotational position in which a graduation is selected, and
wherein the mutually different graduation increments of each of the graduations are exclusively associated with a plurality of longitudinally spaced apart increment formations, and wherein the resilient finger defined by the collar is configured to periodically engage the increment formations of the respective plurality of increment formations associated with a respective selected graduation when the plunger is slid into and out of the barrel during use.

9. The syringe of claim 5, wherein at least one of the at least one first formation and the at least one second formation is resilient, such that the at least one first formation and the at least one second formation are configured to engage one another in a snap type action when the plunger is rotated around the longitudinal axis.

10. The syringe according to claim 1, wherein the mutually different graduation increments of each of the graduations are exclusively associated with a plurality of longitudinally spaced apart increment formations, wherein the pluralities are defined by one of the barrel assembly and the plunger; and
wherein the other of the barrel assembly and the plunger defines an index formation that is configured to periodically engage the increment formations associated with a respective selected graduation when the plunger is slid into and out of the barrel during use, so as to periodically vary resistance to the longitudinally sliding motion and/or to periodically produce an audible sound.

11. The syringe according to claim 10, wherein the increment formations of each plurality of increment formations are equidistantly spaced apart, such that a longitudinal distance between any two adjacent increment formations of a respective plurality of increment formations corresponds to an integer multiple or integer fraction of a graduation increment of the associated graduation.

12. The syringe according to claim 10, wherein the syringe is arranged so the that plunger can move backwardly to at least some extent after a user, who has pushed the plunger forwardly until the index formation engaged a subsequent increment formation during use of the syringe, releases the plunger.

13. The syringe according to claim 12, wherein a length along which the plunger is to be moved backwardly is smaller than 25%, smaller than 15%, smaller than 10%, or at most 5%, of a length between two adjacent increment formations seen in the axial direction of the syringe, wherein said length between said two adjacent increment formations is a length between two adjacent increment formations of the respective plurality of increment formations being engaged by the index formation.

14. The syringe according to claim 10, wherein the index formation is movable with respect to the barrel body in at least a direction parallel to the longitudinal axis.

15. The syringe according to claim 13, wherein a length along which the index formation is movable is smaller than 25%, smaller than 15%, smaller than 10%, or at most 5%, of a length between two adjacent increment formations seen in the axial direction of the syringe, wherein said length between two adjacent increment formations is a length between two adjacent increment formations of that one of the pluralities of longitudinally spaced apart increment formations in which the increment formations are mutually spaced apart the least far.

16. The syringe according to claim 14, wherein the index formation being movable with respect to the barrel body is due to the index formation being formed as a part of an index formation holding portion which is movably held in the collar.

17. The syringe according to claim 14, wherein the index formation being movable with respect to the barrel body is due to the index formation being provided at the collar and said collar being axially movably connected to the barrel body.

18. The syringe according to claim 1, wherein the collar is opaque.

19. The syringe according to claim 1, wherein the plunger further comprises a volume unit indication portion that provides, for each of the at least two graduations, a visually readable volume unit indication that is arranged in longitudinal alignment with the respective graduation.

20. The syringe according to claim 19, wherein each of the at least two graduations includes a plurality of numerical values, such that, when a certain graduation is selected, the numerical value of the selected graduation that is visible through the reading window corresponds to the number of volume units with a volume indicated by the respective volume unit indication that is present in a fluid chamber in the barrel.

21. The syringe according to claim 1, wherein a first one of the at least two mutually different graduations has graduation increments having a first size of 0.01, 0.02, 0.025, 0.04 or 0.05 ml, and wherein a second one of the at least two mutually different graduations has graduation increments that have a second size of 0.01, 0.02, 0.025, 0.04 or 0.05 ml, wherein said second size is different from said first size.

22. The syringe according to claim 1, wherein the at least two mutually different visually readable graduations are provided in mutually different colors.

23. A syringe having a longitudinal axis, comprising:
a barrel assembly including:
   a barrel, extending longitudinally between a proximal end and a distal end,
   a collar, provided at the proximal end of the barrel, and defining a reading window;
a plunger including:
a longitudinally extending graduation portion that is at least partially longitudinally slidably received in the barrel, and that provides for at least two mutually different visually readable graduations, wherein respective graduations extend along the longitudinal axis and are alternatively selectable by rotation of the graduation portion around the longitudinal axis, such that a selected graduation is visible through the reading window when the plunger is slid into and out of the barrel during use,
the syringe further comprising
at least one longitudinally extending first formation defined by one of the barrel assembly and the plunger; and
at least one second formation defined by the other of the barrel assembly and the plunger,
   wherein said first and second formations are configured to engage one another when the plunger is rotated around the longitudinal axis, into a rotational position in which a graduation is selected, so as to releasably lock the plunger in the respective rotational position, and
wherein at least one of the at least one first formation and the at least one second formation is resilient, such that the at least one first formation and the at least one second formation are configured to engage one another in a snap type action when the plunger is rotated around the longitudinal axis, into a rotational position in which a graduation is selected, so as to releasably lock the plunger in the respective rotational position.

* * * * *